US00RE44345E

(19) United States
(12) Reissued Patent
Ackermann et al.

(10) Patent Number: US RE44,345 E
(45) Date of Reissued Patent: Jul. 9, 2013

(54) HOST APPARATUS AND METHOD PROVIDING CALIBRATION AND REAGENT INFORMATION TO A MEASUREMENT APPARATUS WHICH MAKES USE OF A CONSUMABLE REAGENT IN A MEASURING PROCESS

(75) Inventors: Friedrich Karl Ackermann, Heidelberg (DE); Manfred Augstein, Mannheim (DE); Timothy L. Beck, Pendleton, IN (US); Markus Stephan Fuerst, Heddesheim (DE); Robert Lawrence Meek, Indianapolis, IN (US); Philip Edgar Pash, Indianapolis, IN (US); Blaine Edward Ramey, Indianapolis, IN (US); Robert Paul Sabo, Indianapolis, IN (US); Matthew Carlyle Sauers, Indianapolis, IN (US); Joerg Schreiber, Indianapolis, IN (US); Wolfgang Walter, Lobbach (DE); Seth Faulkner Williams, Noblesville, IN (US); Frederick Leland Wittekind, III, Anderson, IN (US)

(73) Assignees: Roche Diagnostics Operations, Inc., Indianapolis, IN (US); Roche Operations Ltd., Hamilton (BM)

(21) Appl. No.: 13/362,011

(22) Filed: Jan. 31, 2012

Related U.S. Patent Documents

Reissue of:

(64) Patent No.: 7,883,015
Issued: Feb. 8, 2011
Appl. No.: 11/914,405
PCT Filed: May 16, 2006
PCT No.: PCT/EP2006/004579
§ 371 (c)(1),
(2), (4) Date: Nov. 14, 2007
PCT Pub. No.: WO2006/122741
PCT Pub. Date: Nov. 23, 2006

(51) Int. Cl.
*G06K 7/00* (2006.01)

(52) U.S. Cl.
USPC ..... 235/439; 235/472.01; 600/300; 600/301; 702/30

(58) Field of Classification Search
USPC ..... 235/439, 472.01; 600/300, 301; 702/30
See application file for complete search history.

(56) References Cited

U.S. PATENT DOCUMENTS

| | | | |
|---|---|---|---|
| 4,686,624 | A | 8/1987 | Blum et al. |
| 4,731,726 | A | 3/1988 | Allen, III |
| 4,803,625 | A | 2/1989 | Fu et al. |
| 5,019,974 | A | 5/1991 | Beckers |
| 5,307,263 | A | 4/1994 | Brown |
| 5,642,731 | A | 7/1997 | Kehr |

(Continued)

FOREIGN PATENT DOCUMENTS

| | | | |
|---|---|---|---|
| DE | 4312093 | A1 | 10/1993 |
| EP | 0 922 959 | A1 | 6/1999 |

(Continued)

*Primary Examiner* — Sally Merkling
(74) *Attorney, Agent, or Firm* — Dinsmore & Shohl LLP

(57) ABSTRACT

Apparatuses and methods providing data such as, for example, calibration and reagent information (30) over a network (6) to a measurement apparatus (4) which makes use of a consumable reagent (18) in a measuring process are disclosed. The present invention permits a measurement apparatus (4) to download the necessary code assignment (24) and calibration data (32) of the consumable reagent (18) by means of an electronic communication protocol from a host (33). The host (33) can be a software application running on a host computer (34), another measurement apparatus (50, 58) with or without a code-key slot used to read a memory device providing the above mentioned information (30), a dedicated connectivity device, such as a docking station (44), a portable memory reader (48), a remote computer (54), and combinations thereof.

58 Claims, 5 Drawing Sheets

U.S. PATENT DOCUMENTS

| | | | | |
|---|---|---|---|---|
| 5,678,571 | A | 10/1997 | Brown | |
| 5,701,894 | A | 12/1997 | Cherry et al. | |
| 5,791,344 | A | 8/1998 | Schulman et al. | |
| 5,822,715 | A | 10/1998 | Worthington et al. | |
| 5,827,180 | A | 10/1998 | Goodman | |
| 5,897,493 | A | 4/1999 | Brown | |
| 5,918,603 | A | 7/1999 | Brown | |
| 5,960,403 | A | 9/1999 | Brown | |
| 5,997,476 | A | 12/1999 | Brown | |
| 6,024,699 | A | 2/2000 | Surwit et al. | |
| 6,101,478 | A | 8/2000 | Brown | |
| 6,139,494 | A | 10/2000 | Cairnes | |
| 6,168,563 | B1 | 1/2001 | Brown | |
| 6,223,288 | B1 | 4/2001 | Byrne | |
| 6,248,065 | B1 | 6/2001 | Brown | |
| 6,295,506 | B1 | 9/2001 | Heinonen et al. | |
| 6,377,894 | B1 | 4/2002 | Deweese et al. | |
| 6,413,213 | B1 | 7/2002 | Essenpreis et al. | |
| 6,645,142 | B2 | 11/2003 | Braig et al. | |
| 6,780,645 | B2 | 8/2004 | Hayter et al. | |
| 7,041,468 | B2 * | 5/2006 | Drucker et al. | 435/14 |
| 2001/0000709 | A1 | 5/2001 | Takahashi et al. | |
| 2002/0019707 | A1 * | 2/2002 | Cohen et al. | 702/30 |
| 2002/0060247 | A1 * | 5/2002 | Krishnaswamy et al. | 235/472.01 |
| 2004/0212344 | A1 * | 10/2004 | Tamura et al. | 320/114 |
| 2006/0167381 | A1 * | 7/2006 | Azer et al. | 600/573 |
| 2008/0139907 | A1 * | 6/2008 | Rao et al. | 600/323 |

FOREIGN PATENT DOCUMENTS

| | | | |
|---|---|---|---|
| JP | 2001521171 | | 11/2001 |
| JP | 2002521692 | | 7/2002 |
| JP | 2005288756 | | 10/2005 |
| WO | 9717012 | | 5/1997 |
| WO | WO 97/29847 | * | 8/1997 |
| WO | 9918532 | | 4/1999 |
| WO | WO 99/22236 | * | 5/1999 |
| WO | 00/07013 | | 2/2000 |
| WO | 02/00112 | | 1/2002 |
| WO | 0200112 A2 | | 1/2002 |
| WO | WO 03/091717 | * | 11/2003 |
| WO | 2006058653 A2 | | 6/2006 |

* cited by examiner

HOST APPARATUS AND METHOD PROVIDING CALIBRATION AND REAGENT INFORMATION TO A MEASUREMENT APPARATUS WHICH MAKES USE OF A CONSUMABLE REAGENT IN A MEASURING PROCESS

Matter enclosed in heavy brackets [ ] appears in the original patent but forms no part of this reissue specification; matter printed in italics indicates the additions made by reissue.

*CROSS-REFERENCE TO RELATED APPLICATIONS*

*This application is a national stage application of PCT/EP2006/004579, filed on May 16, 2006, and claims the benefit of U.S. provisional Application No. 60/744,805, filed on Apr. 13, 2006, and U.S. provisional Application No. 60/681,686, filed on May 17, 2005.*

The present invention relates to measurement systems and methods thereof, and in particular to a host apparatus and method providing calibration and reagent information to a measurement apparatus which makes use of a consumable reagent in a measuring process.

A hospital blood glucose meter is designed to measure the level of glucose in a sample of a patient's blood by use of a consumable reagent. Consumable reagents are generally of a chemical, biochemical, or biological nature. A small amount of a suitable consumable reagent is provided on a disposable test strip. In use, a test strip is inserted into the blood glucose meter, and a sample of the patient's blood, provided to the test strip, reacts with the consumable reagent. The meter, which comprises a calibrated measuring system, measures a property of the reaction between the reagent and the blood sample to determine the amount of glucose present in the blood sample.

It will be appreciated that in the case of a hospital blood glucose meter, where treatment is determined based on the blood glucose measurements, the accuracy of the meter is critical. This requires very precise calibration of the meter. It is known to provide disposable blood glucose test strips, or rather a package of such test strips, with a machine-readable memory on which calibration data is stored.

The current methodology on how calibration data is provided to hospital blood glucose meters requires a nurse to take the machine-readable memory out of the test strip package and insert it in a machine-readable memory slot of the hospital blood glucose meter. The nurse then verifies at each measurement that the lot identification code from the machine-readable memory, which is read and displayed by the meter, matches the package lot number of the test strip actually being used. To perform this task, the nurse scans in with the meter a barcode either provided on the test strip package, or verifies that the displayed barcode matches the printed lot number on the package. This methodology causes several problems. For example, the hospital blood glucose meter must have a machine-readable memory slot, which increases the size of the meter, increases manufacturing costs of the meter, and allows liquid (cleaners) to enter the housing of the meter. Additionally, should the lot numbers of the test strip package in use and the machine-readable memory not match, such as in the case where the machine-readable memory is misplaced; there is no easy way to recover. This invites operators to ignore this mismatch and proceed with the measurement, potentially leading to medical errors.

It is against the above background that the present invention provides a host apparatus and method providing data such as, for example, calibration data and reagent information to a measurement apparatus by means of connectivity over a network. The present invention permits the measurement apparatus to download the necessary calibration data and reagent information by means of an appropriate electronic communication protocol from the host apparatus. Such calibration data and reagent information can be either lot specific or generic. Depending on the embodiment of the invention, the host apparatus can be a computer/server of the point-of-care center (POCC), such as a data manger system (DMS), another measurement apparatus using the same calibration data and reagent information, a dedicated connectivity device, a portable memory reader, and combinations thereof.

In one embodiment, provided is a measurement system comprising a network; a measurement apparatus provided with a first set of lot identification codes, said measurement apparatus is configured to use a consumable reagent in a measurement process, said consumable reagent having an associated lot identification code, said measurement apparatus is configured to transmit over said network said associated lot identification code of said consumable reagent when said associated lot identification code fails to match any of said first set of lot identification codes; and a host apparatus provided with a second set of lot identification codes each having at least calibration data associated therewith, said host apparatus is configured to receive said associated lot identification code of said consumable reagent transmitted from said measurement apparatus over said network, to subsequently identify whether the received said associated lot identification code matches any of said second set of lot identification codes, and to provide at least said at least calibration data associated with a lot identification code in said second set of lot identification codes matching said associated lot identification code to said measurement apparatus over said network.

In another embodiment, provided is a method of deriving a test result using a measurement apparatus and a consumable reagent, the method comprising providing a network; providing a host apparatus with a first set of lot identification codes each having at least calibration data associated therewith; providing a consumable reagent together with an associated lot identification code; providing said measurement apparatus with a second set of lot identification codes; reading said associated lot identification code with said measurement apparatus; transmitting over said network said associated lot identification code of said consumable reagent to said host apparatus when said associated lot identification code fails to match any of said second set of lot identification codes; identifying with said host apparatus whether the received said associated lot identification code matches any of said first set of lot identification codes; providing at least said at least calibration data associated with a lot identification code in said first set of lot identification codes matching said associated lot identification code to said measurement apparatus over said network; and deriving the test result using the measurement apparatus, the consumable reagent, and the calibration data associated with said associated lot identification code received from the host apparatus.

In still another embodiment, provided is a measurement system comprising a removable machine-readable memory containing a lot identification code associated with a consumable reagent; a lot identification code removable machine-readable memory reader configured to read said lot identification code of said consumable reagent from said removable machine-readable memory; measurement apparatus configured to use said consumable reagent in a measurement process, wherein said measurement apparatus is configured to communicate with said lot identification code reader to receive said lot identification code associated with said consumable reagent.

These and other features and advantages of the invention will be more fully understood from the following description of various embodiments of the invention taken together with the accompanying drawings.

The following detailed description of the embodiments of the present invention can be best understood when read in conjunction with the following drawings and in which.

Figure 1:
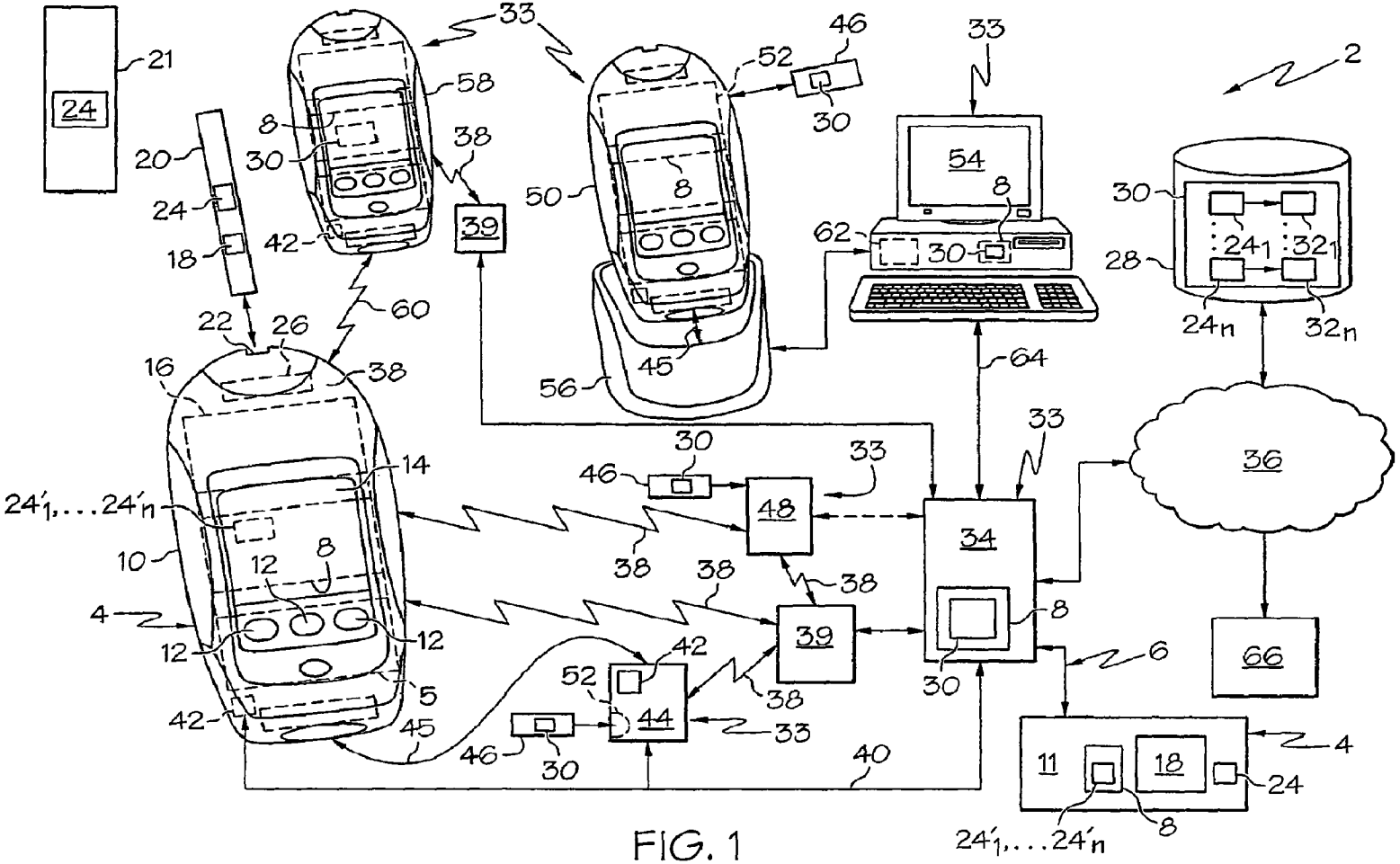
FIG. 1 shows a measurement system embodying the present invention.

FIG. 1 illustrates a point-of-care center (POCC) measurement system, generally indicated by the symbol 2, which is capable of providing calibration and other data to a measurement apparatus, generally indicated by symbol 4, which makes use of a consumable reagent in a measuring process, over a hospital's and other medical institution's network, generally indicated as symbol 6, as will be explained in detail below. The measurement apparatus 4 is also capable of sending data over the network 6 as will also be explained below. It will be appreciated that the system 2 may vary as to configuration and as to details of the parts, and that the method may vary as to specific steps and sequences, without departing from the basic concepts as disclosed herein.

In one embodiment, the measurement apparatus 4 is a handheld diagnostic device 10, such as for example, a hospital blood glucose meter. In other embodiments, the handheld diagnostic device 10 is any other medical diagnostic device that uses a consumable reagent and requires periodic calibration data updates. In still another embodiment, the measurement apparatus 4 is a clinical chemistry analyzer 11 which uses a consumable reagent and requires periodic calibration data updates. In the following discussion, it is to be appreciated that the following system and method embodiments relate equally to the handheld diagnostic device 10 and analyzer 11, and as such, only the handheld diagnostic device 10 is discussed hereafter in greater detail.

In one specific and illustrated embodiment, the measurement system 2 comprises a handheld diagnostic device 10 having a microprocessor 5, memory 8, a keypad 12, a display 14, and a battery unit (not shown) for powering the device. It is to be appreciated that the keypad 12 and display 14 can be one in the same such as, for example, a touch screen. The device 10 also contains an internally arranged measuring system 16 which is configured to use a consumable reagent 18 to measure an analyte such as, for example, glucose in a fluid (i.e., blood) sample from a patient under testing. The consumable reagent 18 is provided to a test carrier such as, for example, a test strip 20, which may be elongated. The test carrier can also comprise a cassette, a cartridge, or any other suitable test carrier. The test strip 20, in use, is inserted into a slot 22 provided in the device 10 and which provides access to the measuring system 16.

In one embodiment, the measuring system 16, the consumable reagent 18, and the test strip 20 are of the type where the microprocessor 5 determines that the test strip 20 is properly inserted in the device 10, and that the excitation and sense electrodes (not shown) of the test strip 20 exhibit proper electrode continuities. Before blood is provided to the reagent 18, the microprocessor 5 causes an excitation voltage source to apply an excitation voltage level to the excitation electrode. Next, the patient's blood is provided to the reagent 18. In one embodiment, the test strip 20 employs capillarity to draw whole blood into the test strip 20 and to the reagent 18, and in another embodiment, the test strip 20 may have a well in which a drop of blood is provided to the reagent 18.

In one illustrative embodiment, the reagent 18 is potassium ferricyanide. The glucose within a blood sample provided to the reagent 18 causes a forward reaction of potassium ferricyanide to potassium ferrocyanide. The forward reaction proceeds to completion during an incubation period. A subsequent application of an excitation voltage to the excitation electrode in the test strip 20 will cause the creation of a small current at a sense electrode that results from a reverse reaction of potassium ferrocyanide back to potassium ferricyanide. The flow of electrons during the reverse reaction is sensed and measured by the device 10 at a number of points to enable a determination that the reaction is following a Cottrell curve and to further determine the level of the Cottrell curve, which is indicative of the glucose concentration on the blood sample. The resultant glucose value, thereafter corrected to take into account ambient temperature, is then provided as the amount of glucose present in the blood sample. Such a blood glucose measuring method, consumable reagent 18, and test strip 20 are described in greater detail by, for example, commonly assigned U.S. Pat. Nos. 5,352,351 and 5,366,609, the disclosures of which are herein fully incorporated by reference. It is to be appreciated, however, the system and method of the present invention is equally applicable to a reflectometry based measuring system, in addition to an electrolytic based measuring system, or any other suitable testing system that uses a consumable reagent requiring manufacturer calibration data.

In addition to the consumable reagent 18, the test strip 20 and a container 21, which the test strips 20 are provided from or both, may be optionally provided with an identification code 24. The identification code 24 is the manufacturing lot number of the test strip 20. It is to be appreciated that the lot identification code 24 can extend to one or more test strip lots. The identification code 24 may be represented in such a way that it may be read visually, or at least by one of an optical-, magnetic-, RF-, or electrically-based identification code reader 26. In such an embodiment, the handheld diagnostic device 10 contains a suitable identification code reader 26, aligned with the slot 22, which reads the identification code 24 when the test strip 20 is inserted into the slot 22. The use of the identification code 24 is explained more fully in the discussion of the various embodiments that follow hereafter.

The manufacturer or distributor of the test strips 20 maintains a central database 28 containing a lot data file 30 containing a set of identification codes $\mathbf{24}_1, \ldots \mathbf{24}_n$ which are each associated with a respective set of calibration data $\mathbf{32}_1, \ldots \mathbf{32}_n$. For a reflectometry based measuring system, the calibration data $\mathbf{32}_1, \ldots \mathbf{32}_n$ typically includes an offset value and a scaling factor which can be used to relate a measured color change to a blood glucose level (non-linear calibration data may also be provided). For an electrolytic based measuring system, the calibration data $\mathbf{32}_1, \ldots \mathbf{32}_n$ typically includes definition of test sequence (start and end times), measurement delay times, an incubation time, the number of measurements to be taken during a measurement period, various thresholds against which voltage levels are to be compared, values of excitation voltage levels to be applied to a sample strip during a test procedure, glucose value conversion factors, and a variety of failsafe test threshold values. The calibration data $32_1, \ldots 32_n$ for each test strip lot is initially determined following manufacture of the lot, for example by comparing the results of a test carried out using a typical measurement unit and by laboratory analysis. The calibration data $32_1, \ldots 32_n$, however, is updated at regular time intervals by re-testing samples taken from a retained test strip stock for each lot.

The handheld diagnostic device 10 downloads the lot data file 30 from the system 2 by means of some appropriate electronic communication protocol from a host, generally indicated by symbol 33, to access the necessary calibration data $32_1, \ldots 32_n$, which can be specific to one or more lots. The host 33 from which the lot data file 30 may be accessed and downloaded by the device 10 depends on the networking environment. For example, in one embodiment, the host 33 is a computer system of the POCC, such as, for example, a data manager system (DMS) 34 that receives the lot data file 30 from the central database 28 via the Internet 36. The DMS 34 then distributes the lot data file 30 to the device 10 via a wireless network 38 or a wired network 40. The network connection of the device 10 in one embodiment is provided through an included network interface device 42, which may be wire or wireless based. The wireless network 38 is conventional and may provide access points 39 throughout the POCC to facilitate the wireless network connection to the DMS 34.

In another embodiment, the device 10 connects to a networked docking station 44 having the network interface device 42. In such an embodiment, the device 10 connects to the networked docking station 44 using a provided data and power connector 45 to interface with the wired network 40 or the wireless network 38, via the network interface device 42.

In another embodiment, the lot data file 30 is provided and shipped in a removable machine-readable memory 46 with the package of disposable test strips, and loaded into the DMS 34 via a lot identification code reader 48, and then distributed to the device 10 via the wireless network 38 or wired network 40. In still another embodiment, the lot identification code reader 48 is portable and configured to communicate wirelessly the lot data file 30 contained in the removable machine-readable memory 46 with the device 10. In such an embodiment, the lot identification code reader 48 may also communicate the lot data file 30 contained in the removable machine-readable memory 46 to the DMS 34, the remote workstation 54, and the other devices 50, 58 via the wireless network 38 and/or the wired network 40.

In yet another embodiment, the host 33 may be a conventional device 50, such as a hospital blood glucose meter with a machine-readable memory slot 52. In this embodiment, the machine-readable memory 46 containing the lot data file 30 is placed in the machine-readable memory slot 52 and transferred to a remote station 54 via an attached docking station 56. The lot data file 30 is then provided to the device 10 either by connecting the device 10 to the docking station 56 or by the remote station 54 providing the lot data file 30 to the DMS 34, which redistributes the lot data file 30 to the device 10 via the wireless network 38 or the wired network 40. It is to be appreciated, in another embodiment, the docking station 44 may be provided with the machine-readable memory slot 52 for the same above-mentioned purpose.

In still another embodiment, the host 33 can be another hospital handheld diagnostic device 58 which is provided with the network interface device 42, and which serves as a host for the device 10, and communicates over the wireless network 38 or via peer-to-peer connection 60 (wired or wireless, for example, infrared based communications). In one embodiment, the handheld diagnostic device 58 is the same type of device as device 10, such as both being a pair of blood glucose meters, and in other embodiments device 58 may be a different type of device from device 10 but which still uses a consumable reagent and requires calibration data. Accordingly, in view of all the above host embodiments, it is to be appreciated that the communication of the lot data file 30 over the system 2 is determined by the configuration of the system and/or the network environment in which the device 10 is presently located, and which the various embodiments thereof are discussed in greater detail in later sections in reference to FIGS. 3-6.

In FIG. 1, it is also to be appreciated that measurement data may be communicated to the DMS 34 and/or the remote station 54 at the time the measurement is performed, or it may be retained within the device 10 and sent to the DMS 34 and/or the remote station 54 according to a schedule or other selection criterion. The measurement data can be routed from the device 10 through the in-building wireless network 38 to the DMS 34, or via one of the docking station 44 or 56. As illustrated, docking station 56 is directly connected via I/O port 62 to the remote station 54, which may be programmed to provide updates to the DMS 34, via network connection 64.

The DMS 34 is capable of checking the data for emergency conditions and logging the data for later use. In addition, the DMS 34 may monitor equipment status for proper operation and calibration. It will be appreciated that multiple servers, or centralized stations, such as remote station 54, can be provided for communicating with the handheld diagnostic devices. Furthermore, the DMS 34 may transfer or simultaneously route the data via connection 64 to remote station 54, or an external computer 66 in the office of a medical practitioner over the Internet 36. It will be appreciated that the foregoing data routing is provided as an example, and not as a limitation, of the data routing utilized to provide the services as described according to the invention.

Figure 2:
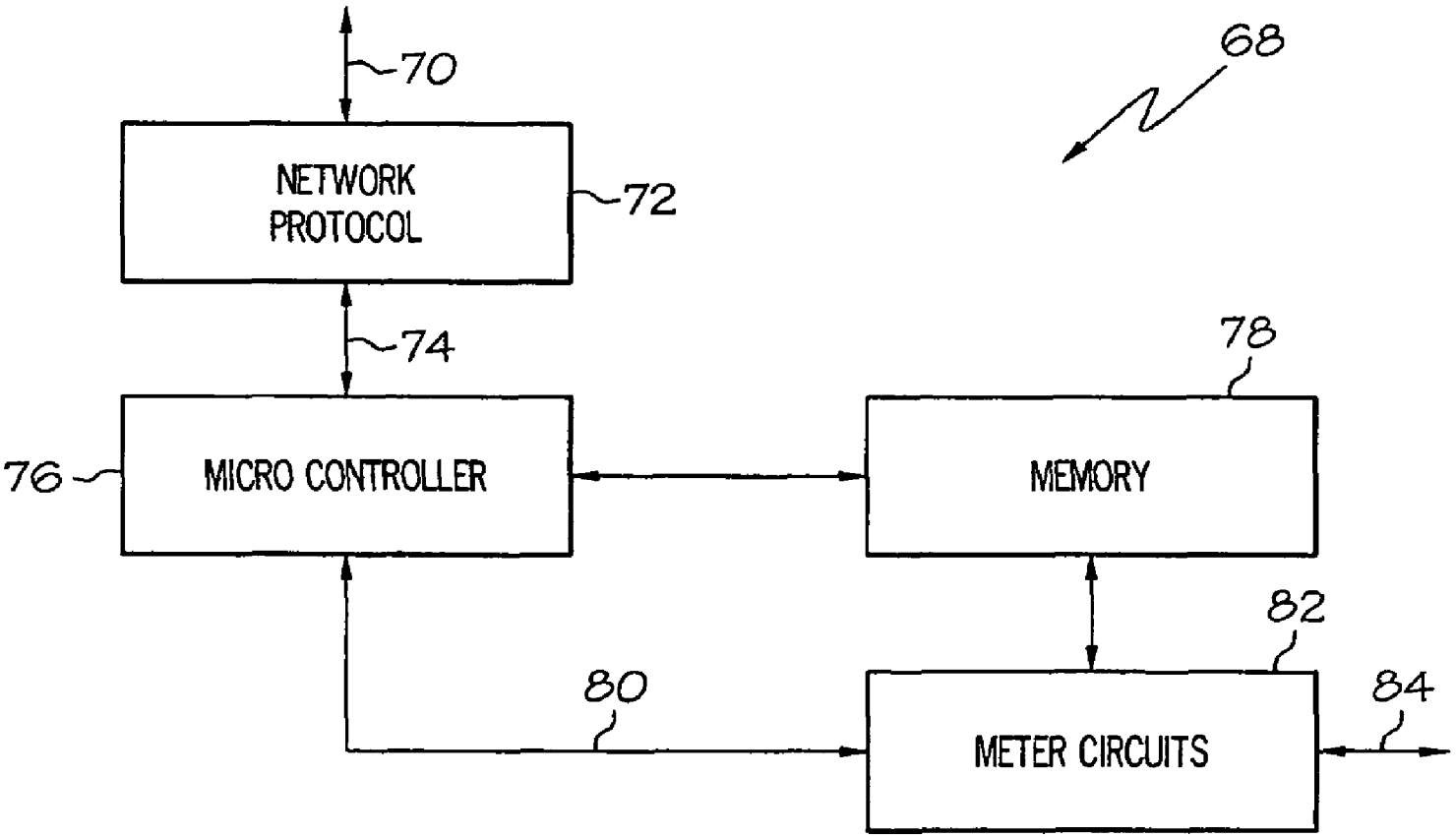
FIG. 2 illustrates functional blocks of an embodiment of circuitry for implementing the communications shown in FIG. 1.

FIG. 2 illustrates the functional blocks of an embodiment of circuitry 68 for implementing the communications shown in FIG. 1, and discussed previously above. A network connection 70 connects to a network processing circuit. Numerous circuits are available for providing network connectivity, such as in one embodiment to include the network interface stacks as part of the firmware running on a microcontroller 76. In still another embodiment, a separate network processor 72 may be included for this functionality, such as, for example, the SX-Stack™ chip from Scenix Semiconductor, and the iChip™ from Connect One Electronics. These integrated circuits and other available chips provide interface layers for supporting a Transmission Control Protocol/Internet Protocol (TCP/IP). TCP/IP is only mentioned as an example, however it is to be appreciated that any other network transport protocol would be equally applicable to the present invention. In the latter embodiment, the network protocol processor 72 has an interface 74 with the microcontroller 76 having access to conventional memory 78. To provide security and fault tolerance of the device 10 it is preferable for the microcontroller 76, or the internet protocol processor 72, to encrypt and provide verification strings or tokens within the data being sent across the network, and accordingly to decrypt information being received and verify the received strings or tokens. The microcontroller 76 has an interface 80 with the device circuits 82, which is in turn configured with an interface 84 to the measuring system 16 shown in FIG. 1.

The measurement system 2 provides a mechanism to facilitate performing and recording measurements, such as glucose measurements, while it additionally provides for periodic instrument calibration, and the ability to assure both measurement and calibration compliance. The lot data file 30, with calibration data $32_1, \ldots 32_n$ specific to one or more lots (i.e., lots identified by identification codes $24'_1, \ldots 24'_n$), can be communicated from the instrument manufacturer to instruments in the field, or a service organization, so that instruments and their calibrations may be logged. The disclosed system 2 can be utilized to provide various mechanisms for assuring calibration compliance. The various methods of ensuring the proper calibration data is used in testing of a physical parameter, such as blood glucose level of a patient, are now described hereafter with reference made to FIGS. 1, 3, and 4.

Figure 3:
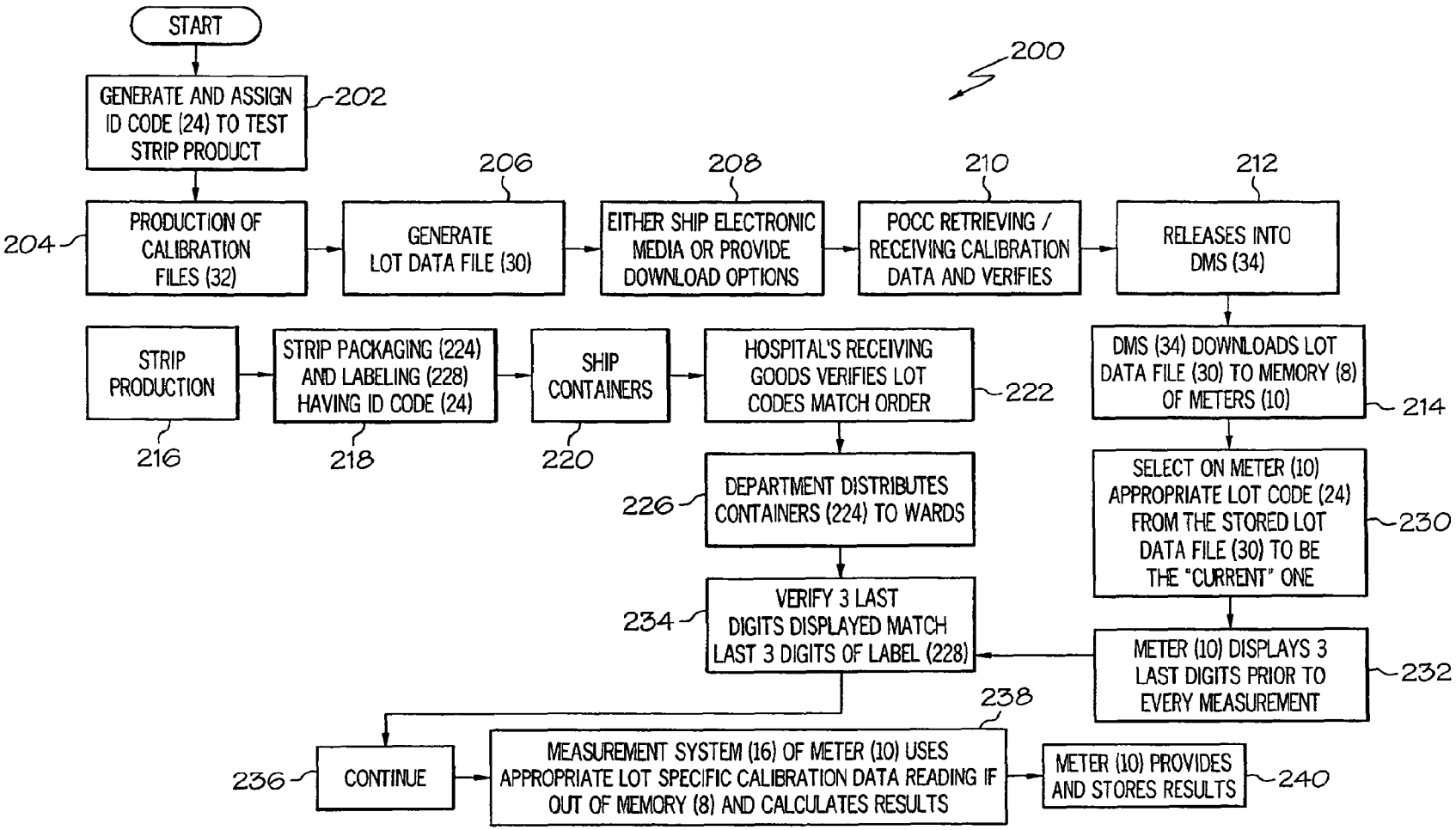
FIG. 3 is a process flow of one embodiment providing at least calibration data to a hospital measurement apparatus.

FIG. 3 illustrates one embodiment of a process 200 for assuring calibration compliance within the device 10 by utilizing the DMS 34 as the host to download current calibration data to the hospital measurement apparatuses 4. At step 202, a lot identification code 24 is generated and assigned to each test strip lot production run. The calibration data 32 for each produced test strip lot are then generated in step 204. A lot data file 30 is generated in step 206, which correlates each lot identification code 24 to the calibration data 32 generated in step 204. In one embodiment shown by FIG. 1, the lot data file 30 contains a set of lot identification codes $24_1, \ldots 24_n$ and their related calibration data $32_1, \ldots 32_n$ for the current and a number of past test strip lots. In one embodiment, the lot data file 30 provides at least the lot identification codes $24_1, \ldots 24_n$ and their related calibration data $32_1, \ldots 32_n$ for the last three test strip lot production runs. In other embodiments, the set may be one to any convenient number of lot identification codes and their associated calibration data.

In step 208, in one embodiment the lot data file 30 is distributed electronically from the central database 28 to the POCC DMS 34 via the Internet 36. It is to be appreciated that the lot data file 30 can be released to the customer by different means, such as, for example, mailing a CD, sending an email, or providing an URL to have the customer downloading the data from the central database 28. One or more of these distribution methods can be chosen, and all of them can be secured in order to ensure confidentiality, integrity, and authenticity of the content in the released lot data file 30.

In one embodiment, the lot data file 32 is encrypted before being sent to the POCC DMS 34 using a standard encryption application. An operator of the POCC DMS 34 decrypts the lot data file 30 using a standard decryption application compatible with the encryption application, if necessary, and in step 210 inspects the lot data file 30 to verify that its lot identification codes 24 match the lot identification codes 24 of the test strips being used at the POCC. Once verified, the operator releases the lot data file 30 into the DMS 34 for general downloading/updating by the measurement apparatuses 4 within the system 2 in step 212. The measurement apparatus 4, such as device 10, analyzer 11, and even other hosts 33, at the next connection time or communication with the DMS 34, will download the lot data file 30 into its memory 8 in step 214.

In parallel with the above mentioned lot data file production steps 202, 204, and 206, test strip lot production and test strip lot packaging and labeling occur in steps 216 and 218, respectively. A test strip order is shipped in step 220 by the manufacturer, which is received and verified by the POCC in step 222. In one embodiment, it is to be appreciated that the lot data file 30 may be sent with the order on a machine-readable memory, such as machine-readable memory 46 illustrated in FIG. 1. After lot identification code verification in step 222 (or step 210), the POCC distributes the disposable test strips throughout the necessary wards, typically packaged in a container 224 holding a quantity of test strip in step 226. It is to be appreciated that each container 224 has a label 228 that at least identifies an expiration date, and the assigned lot identification code 24. The process 200 then proceeds hereafter with the use of the device 10, such as during a blood glucose test.

In the illustrated embodiment, where the device 10 is a hospital blood glucose meter, to initiate a blood glucose test, the nurse activates a measurement sequence using a menu displayed on the handheld diagnostic device's display 14. In the embodiment illustrated by FIG. 3, from the menu displayed, the nurse will select one of the available lot identification codes $24_1', \ldots 24_n'$ read from the memory 8 of the device 10 to be the "current" lot identification code in step 230. After selection of the current lot identification code, the device 10 in step 232 will display a portion (e.g., the last three digits) of the current lot identification code prior to every blood glucose test, which is initiated by insertion of a disposable test strip into slot 22. Prior to insertion, the nurse deposits a small amount of blood from a patient on top of the reagent 18 provided on the test strip 20. After a short time, the test strip 20 is fully inserted into the slot 22. Upon insertion, the nurse then will be prompted by the device 10 at each measurement to verify, that the displayed portion of the current lot identification code matches with same portion of the lot identification code provided on the label 228 of the container 226 from which the disposable test strip 20 was drawn in step 234. Relying on this verification, and acknowledged by the nurse selecting to continue with the testing from the displayed prompt provided on the device 10 in step 236, the measuring system 16 will determine the change in the reagent 18 in step 238.

The handheld diagnostic device 10 then proceeds to calculate a blood glucose test result using the measured change of the reagent 18, the calibration data 32, which is read from the lot data file 30 stored in memory 8 and which corresponds to the selected current lot identification code 24, and a calculation algorithm which is pre-stored and read from also memory 8. This calculation is carried out by the microprocessor 5 of the handheld diagnostic device 10. The result is then displayed on the display 14 in step 240, and also stored on the device's memory 8.

Figure 4A:
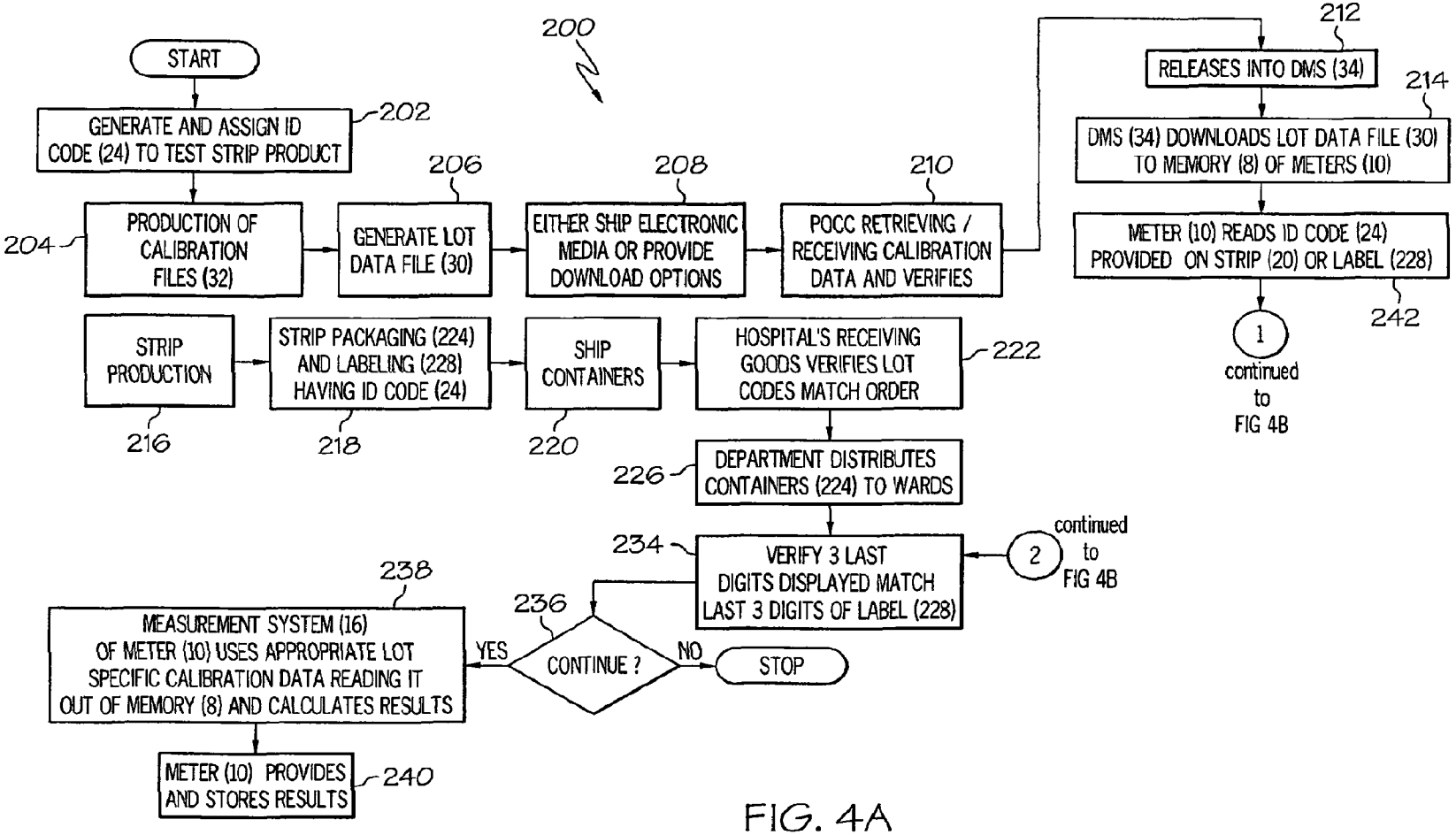
FIG. 4 is a process flow of another embodiment providing at least calibration data to a hospital measurement apparatus.
Figure 4B:
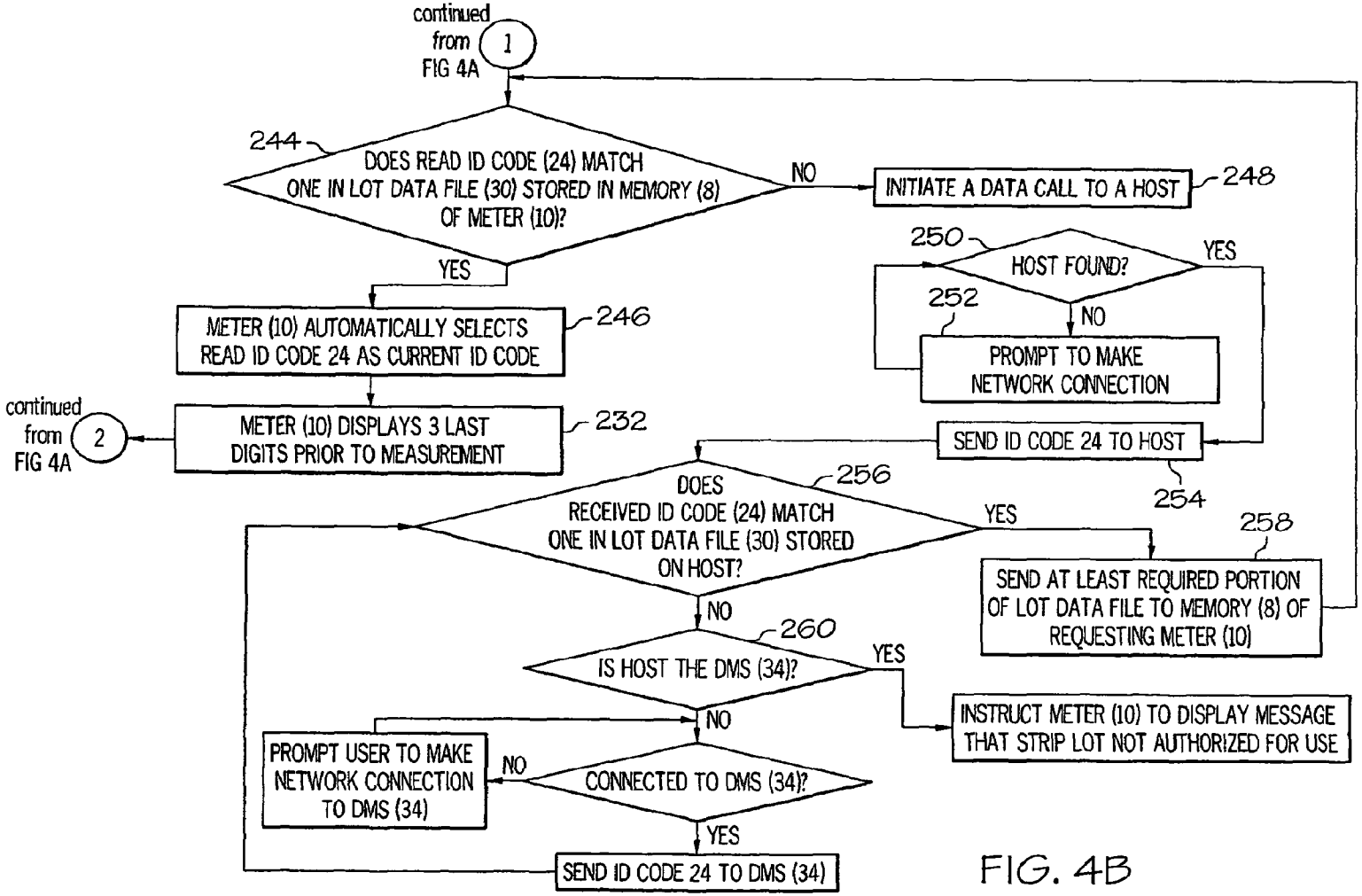

Another embodiment is illustrated by FIG. 4, in which like steps discussed in regards to FIG. 3 are indicated with like numbers and thus, for convenience of brevity, only the differences between the embodiments are discussed hereafter. In the situation where a strip's lot identification code 24 is provided on the test strip 20, the device 10 will read the identification code 24 using the included identification code reader 26 upon insertion of the strip 20 into the device 10, via slot 22, in step 242. In an alternative embodiment, the nurse scans the label 228 with the identification code reader 26 of the device 10 to read the strip's lot identification code 24 in step 242.

Next, in step 244, the device 10 checks to see if the read lot identification code 24 matches a lot identification code $24_1', \ldots 24_n'$ provided in the stored lot data file 30 in memory 8. If the read lot identification code 24 matches one of the lot identification codes $24_1', \ldots 24_n'$ provided in the stored lot data file 30 of the device 10, then the device will select automatically the read lot identification code 24 as the current lot identification code, in step 246. If in step 244 the read lot identification code 24 does not match up with one of the lot identification code $24_1', \ldots 24_n'$ contained in the lot data file 30 stored in the memory 8 of the device 10, then in step 248 the device 10 initiates automatically a data call to a host 33 available on the system 2 for an update.

As mentioned above, the host 33 depending on the system environment may be the docking station 44, another hospital handheld diagnostic device 50 or 58, a remote station 54, and/or the DMS 34. Accordingly, in one embodiment, the host 33 is another hospital handheld diagnostic device from which the device 10 receives at least the necessary calibration data specific to one or more lots. In one embodiment, the connection between devices 10, 50, and 58 is a direct connection, and in another embodiment, the connection between devices 10, 50, and 58 is an indirect connection having at least one intermediary device passing the data therebetween. In another embodiment, the host 33 is a dedicated connectivity device 44, 48, or 50 with the machine readable memory slot 52 loaded with the machine readable memory 46 from which the device 10 received at least the necessary calibration data, either directly or indirectly, e.g. through the remote station 54, wired network 40, or wireless network 38. In still another embodiment, the host 33 is a computer system of the POCC, such as, for example, the DMS 34, and the device receives at least the calibration data through a connection 38, 40, or 56 to the DMS 34.

In step 250, the device 10 checks to see if a host 33 is found. If the device 10 fails to connect to a host 33, then in step 252 the device 10 prompts the nurse by a message displayed on the handheld diagnostic device's display 14 to initiate a data call to a host 33 of the system 2. Following acceptance of the prompt by the nurse in step 252, finding and connecting to a host 33 in step 250, the handheld diagnostic device 10 transmits the read lot identification code 24 to the available host in step 254. In step 256, the available host responds by checking to see if the received lot identification code 24 matches one of the lot identification codes $\mathbf{24}_1, \ldots \mathbf{24}_n$ contained in its stored lot data file 30. If there is a match in step 256, then the host transmits back the updated lot data file 30 or at least the needed calibration data 32 to the handheld diagnostic device 10 via the system 2 in step 258. The process then continues at step 246 as mentioned above in regards to FIG. 3.

If there is not a match in step 256, then the host 33 checks to see if it is the DMS 34 in step 260. As only verified and authorized lots have been released to the wards, if the forwarded lot identification code does not match one of the lot identification codes $\mathbf{24}_1, \ldots \mathbf{24}_n$ in a lot data file 30 provided on the DMS 34, a message indicating that the test strip lot is not authorized for use will be sent to the device 10 requesting the updated lot data file from the DMS 34 in step 262. A similar message may be sent to a designated personnel such that corrective action may be taken to determine why the test strip is unauthorized for use, such as in the case of expired lots or non-released/unverified lots that may have been mistakenly distributed.

If in step 260, the host 33 is not the DMS 34, then the host checks to see if it is connected to the DMS 34 in step 264. If the host 33 is not connected to the DMS 34, then a message is displayed on the device and/or host 33 to connect directly to the DMS 34 for updating in step 266. After connecting to the DMS 34, then in step 268 the device or host will forward the received lot identification code to the DMS 34 for checking, as a new or updated lot data file 30 received from the central database 28 may be available for downloading from the DMS 34. The process then continues at step 256 as explained previously above, except with the host being the DMS 34, and continues thereafter with the process steps as explained above in reference to FIG. 3.

It is to be appreciated that in the case of expired lots, in one embodiment the device 10 and hosts 33 are programmed to delete certain lot identification codes from the available lot data file 30 on the network past an expiration date provided in the lot date file. In this manner, after the expiration date, the above-mentioned "unauthorized for use" message in step 262 will be displayed on the device 10. In another embodiment, the device 10 can check an expiration date provided in the lot data file 30 corresponding to the read lot identification code 24, and if the current date provided by an internal clock of the device is past the expiration date, the device will not perform the blood glucose test, and will provide a message to the nurse that the test strip lot is expired.

It is to be appreciated that the result provided in step 240 can be obtained by transmitting the measured change from the handheld diagnostic device 10 to one of the hosts 34, 44, 48, 50, 54, 58, together with the lot identification code 24. The available host 33 can then process the measured value using the calibration data from the lot data file 30 to generate a test result. It is then not necessary to transmit the calibration data to the handheld diagnostic device 10 and only the test result needs to be transmitted. The result received by the handheld diagnostic device 10 can then be displayed directly on the handheld diagnostic device's display.

It is further to be appreciated that in order to maximize the benefit for the customer the above mentioned embodiments may be combined in any one of a number of combinations. Also, it is to be appreciated that sending the calibration data to the hospital handheld diagnostic device 10 by means of electronic data communication instead of providing a machine readable memory 46 results in increased reliability by ensuring that the most up to date calibration data is used in the measurement system 2 before performing a blood test with the device 10.

In addition to providing the measurement system 2 with the most up to date calibration data at the time of a blood test, the system provides a number of other significant advantages. For example, it is to be appreciated that the present invention allows building a hospital handheld diagnostic device without a machine readable memory slot which reduces device costs, eliminates a major reason for device breakages by making it more robust against cleaning and electrostatic discharge, and eliminates one of the most frequent usage errors in the field, i.e. incorrect calibration data. This usage error may cause unnecessarily repeated measurements or medical diagnostic errors. Finally, it is to be appreciated that the present invention is fully compatible with current and future methods of calibration and code assignment, and does not constrain chemistry development and manufacturing of blood glucose strips. Accordingly, the present invention permits a manufacturer to change raw materials and environmental conditions, or even to adapt calibration to special needs in certain countries, without changing the device design.

In view of the above disclosure it is to be appreciated that the present invention, which is directed to providing manufacturer calibration data over a wired or wireless network, has useful applications in handheld and desktop point-of-care or near patient testing systems, as well as in fully-automated, computerized clinical chemistry analyzers 11 (FIG. 1) for the central lab, which use a plurality of consumable reagents 18. Such chemistry analyzers 11 are, for example, the Roche/Hitachi MODULAR ANALYTICS, Roche COBAS Integra and/or Roche COBAS 6000 systems, which are fully automated, software-controlled systems for clinical chemistry and immunoassay analysis that are designed for both quantitative and qualitative in vitro determinations using a large variety of tests for analysis. As the provision of calibration data and other information may be implemented in the same manner as described above for the handheld diagnostic device 10, for convenience, no further discussion is provided.

The above description and drawings are only to be considered illustrative of exemplary embodiments, which achieve the features and advantages of the present invention. Modification and substitutions to specific process steps, system, and setup can be made without departing from the spirit and scope of the present invention. Accordingly, the invention is not to be considered as being limited by the foregoing description and drawings, but is only limited by the scope of the appended claims.

The invention claimed is:

1. A measurement system comprising:

a network;

a measurement apparatus provided with a first set of lot data files containing calibration data and lot identification codes each associated with respective ones of the calibration data, said measurement apparatus uses a consumable reagent in a measurement process, said consumable reagent having an associated lot data file containing calibration data and associated lot identification codes each associated with respective ones of the calibration data, wherein said measurement apparatus transmits over said network said associated lot data file of said consumable reagent when said associated lot identification codes fail to match any of said lot identification codes of the first set of lot data files provided on the measurement apparatus; and a host apparatus provided with a second set of lot data files containing calibration data and lot identification codes each associated with respective ones of the calibration data, said host apparatus receives said associated lot data file containing the associated lot identification codes each associated with respective calibration data of said consumable reagent transmitted from said measurement apparatus over said network, to subsequently identify whether the associated lot identification codes in the received lot data file match any of the lot identification codes of the second set of lot data files, and to distribute said lot data file of said consumable reagent containing the calibration data and the lot identification codes each associated with respective ones of the calibration data via the network when one of said associated lot identification codes matches one of the lot identification codes of the second set of lot data files.

2. The measurement system of claim 1 wherein said network is an in-building wireless network.

3. The measurement system of claim 1 wherein said network is a wired network.

4. The measurement system of claim 1 wherein said network is a peer-to-peer connection.

5. The measurement system of claim 1 wherein said network is selected from a group comprising an in-building wireless network, a wired network, a peer-to-peer connection, and combinations thereof.

6. The measurement system of claim 1 wherein said measurement apparatus is a handheld diagnostic device.

7. The measurement system of claim 1 wherein said measurement apparatus is a clinical chemistry analyzer.

8. The measurement system of claim 1 wherein said measurement apparatus comprises a lot identification code reader which is configured to read said associated lot data file of said consumable reagent.

9. The measurement system of claim 1 wherein said associated lot data file is provided in a machine-readable memory, and said measurement apparatus communicates with a reader for the machine-readable memory which reads said machine-readable memory in order to provide said associated lot data file to said measurement apparatus.

10. The measurement system of claim 1 wherein said measurement apparatus comprises a lot identification code reader which is configured to read said associated lot data file of said consumable reagent, wherein said associated lot data file is a radio frequency identification tag, and said lot identification code reader is a radio frequency identification tag reader.

11. The measurement system of claim 1 wherein said measurement apparatus comprises a lot identification code reader which reads said associated lot data file of said consumable reagent, wherein said associated lot data file is a magnetic identification tag, and said lot identification code reader is a magnetic identification tag reader.

12. The measurement system of claim 1 wherein said measurement apparatus comprises a lot identification code reader which reads said associated lot data file of said consumable reagent, said consumable reagent being provided on a disposable strip and said associated lot data file being provided on a container providing said disposable strip.

13. The measurement system of claim 1 wherein said measurement apparatus comprises a lot identification code reader which reads said associated lot data file of said consumable reagent, said consumable reagent being provided on a disposable strip and said associated lot data file being provided on said disposable strip.

14. The measurement system of claim 1 wherein said host apparatus is a data management system.

15. The measurement system of claim 1 wherein said host apparatus is another measurement apparatus.

16. The measurement system of claim 1 wherein said host apparatus is a computer station.

17. The measurement system of claim 1 wherein said host apparatus is a docking station.

18. The measurement system of claim 1 wherein said host apparatus is a reader for a machine-readable memory removable from one of the reagent, a test strip which provides the reagent, and a container which provides a plurality of test strips.

19. The measurement system of claim 1 wherein said second set of lot data files is provided in memory of said host apparatus, wherein said memory is a machine-readable memory removable from one of the reagent, a test strip which provides the reagent, and a container which provides a plurality of test strips.

20. The measurement system of claim 1 wherein said second set of lot data files is provided in memory of said host apparatus, wherein said memory is a machine readable memory removable from one of the reagent, a test strip which provides the reagent, and a container which provides a plurality of test strips, and said host apparatus is a docking station.

21. The measurement system of claim 1 wherein said host apparatus has access to memory which contains said second set of lot data files.

22. The measurement system of claim 1 further comprising a database in communication with said host apparatus, said database containing said second set of lot data files.

23. The measurement system of claim 1 further comprising a database in communication with said host apparatus over a public network, said database containing said second set of lot data files.

24. The measurement system of claim 1 wherein said measurement apparatus has a display and calculates a test result using calibration data associated with one of said associated lot identification codes and displays said test result on said display.

25. The measurement system of claim 1 wherein said calibration data is specific to one or more lots of a consumable reagent.

26. The measurement system of claim 1 wherein said host apparatus calculates a test result using calibration data associated with one of said lot identification codes in said second set of lot data files, and provides the test result to said measurement apparatus.

27. A method of deriving a test result using a measurement apparatus and a consumable reagent, the method comprising:

providing a network;

providing a consumable reagent together with an associated lot data file containing calibration data and associated identification codes each associated with respective ones of the calibration data;

providing said measurement apparatus with a first set of lot data files containing calibration data and identification codes each associated with respective ones of the calibration data provided therewith;

providing a host apparatus with a second set of lot data files containing calibration data and identification codes each associated with respective ones of the calibration data provided therewith;

reading said associated lot data file of said consumable reagent with said measurement apparatus;

transmitting over said network said associated lot data file of said consumable reagent to said host apparatus when said associated lot identification codes of said consumable reagent fail to match any of said lot identification codes of the first set of lot data files provided on the measuring apparatus;

identifying with said host apparatus whether the associated lot identification codes of the received first set of lot data files match any of the lot identification codes of the second set of lot data files;

distributing said lot data file of said consumable reagent via the network from the host apparatus when one of said associated lot identification codes matches one of the lot identification codes of the second set of lot data files; and deriving the test result using the measurement apparatus, the consumable reagent, and the calibration data associated with said associated lot identification code received from the host apparatus.

28. The method of claim 27 wherein said network is an in-building wireless network.

29. The method of claim 27 wherein said network is a wired network.

30. The method of claim 27 wherein said network is a peer-to-peer connection.

31. The method of claim 27 wherein said network is selected from a group comprising an in-building wireless network, a wired network, a peer-to-peer connection, and combinations thereof.

32. The method of claim 27 wherein said measurement apparatus is a blood glucose meter.

33. The method of claim 27 wherein said measurement apparatus comprises a reader, and said method further comprises reading with said reader said associated lot data file of said consumable reagent.

34. The method of claim 27 wherein said measurement apparatus comprises a lot identification code reader, and said method further comprises reading with said reader an associated lot identification code having at least calibration data associated therewith of said consumable reagent, wherein said associated lot identification code having at least calibration data associated therewith is a barcode, and said lot identification code reader is a barcode reader.

35. The method of claim 27 wherein said measurement apparatus comprises a lot identification code reader, and said method further comprises reading with said reader an associated lot identification code having at least calibration data associated therewith of said consumable reagent, wherein said associated lot identification code having at least calibration data associated therewith is a radio frequency identification tag, and said lot identification code reader is a radio frequency identification tag reader.

36. The method of claim 27 wherein said measurement apparatus comprises a lot identification code reader, and said method further comprises reading with said reader an associated lot identification code having at least calibration data associated therewith of said consumable reagent, wherein said associated lot identification code having at least calibration data associated therewith is a magnetic identification tag, and said lot identification code reader is a magnetic identification tag reader.

37. The method of claim 27 wherein said measurement apparatus comprises a lot identification code reader, and said method further comprises reading with said reader an associated lot identification code having at least calibration data associated therewith of said consumable reagent, said consumable reagent being provided on a disposable strip and said associated lot identification code having at least calibration data associated therewith being provided on a container providing said disposable strip.

38. The method of claim 27 wherein said measurement apparatus comprises a lot identification code reader, and said method further comprises reading with said reader an associated lot identification code having at least calibration data associated therewith of said consumable reagent, said consumable reagent being provided on a disposable strip and said associated lot identification code having at least calibration data associated therewith being provided on said disposable strip.

39. The method of claim 27 wherein said host apparatus is a data management system.

40. The method of claim 27 wherein said host apparatus is another measurement apparatus.

41. The method of claim 27 wherein said host apparatus is a computer station.

42. The method of claim 27 wherein said host apparatus is a docking station.

43. The method of claim 27 wherein said host apparatus is a reader for a machine-readable memory which is removed from one of the reagent, a test strip which provides the reagent, and a container which provides a plurality of test strips.

44. The method of claim 27 further comprises providing said second set of lot data files in memory of said host apparatus, wherein said memory is a removable machine-readable memory removable from one of the reagent, a test strip which provides the reagent, and a container which provides a plurality of test strips.

45. The method of claim 27 further comprises providing said second set of lot data files in memory of said host apparatus, wherein said memory is a removable machine readable memory removable from one of the reagent, a test strip which provides the reagent, and a container which provides a plurality of test strips, and said host apparatus is a docking station.

46. The method of claim 27 further comprising said host apparatus accessing memory which contains said second set of lot data files.

47. The method of claim 27 further comprising said host apparatus communicating with a database, said database containing said second set of lot data files.

48. The method of claim 27 further comprising said host apparatus communicating with a database over a public network, said database containing said second set of lot data files.

49. The method of claim 27 wherein said measurement apparatus has a display and said method further comprises said measurement apparatus calculating a test result using said calibration data associated with said associated lot identification code and displaying said test result on said display.

50. The method if claim 27 wherein if there is not a match between said associated lot identification code with any one of the lot identification codes contained in the first set of lot data files, said method further comprises displaying a message on said measurement apparatus indicating that said reagent is not authorized for use.

51. The method of claim 27 wherein if there is not a match between said associated lot identification code with any one of the lot identification codes contained in the first set of lot data files, said method further comprises displaying a message on said measurement apparatus indicating that said reagent is not authorized for use, and sending a similar message to a designated personnel such that corrected action may be taken.

52. The method of claim 27 wherein said associated lot identification code has an associated expiration date, wherein said method further comprises displaying on said measurement apparatus a message indicating said reagent is unauthorized for use after said expiration date has expired.

53. The method of claim 27 wherein said measurement apparatus is a clinical chemistry analyzer.

54. The method of claim 27 wherein said calibration data is specific to one or more lots of said consumable reagent.

55. A measurement system using a consumable reagent, said system comprising:

a machine-readable memory removable from one of the reagent, a test strip which provides the reagent, and a container which provides a plurality of test strips, said memory containing a lot data associated with a consumable reagent, said lot data file containing calibration data and lot identification codes each associated with respective ones of the calibration data provided therewith;

a reader which interfaces with the machine-readable memory and reads said lot data file of said consumable reagent from said removable machine-readable memory; and a measurement apparatus remote from said reader and which uses said consumable reagent in a measurement process, wherein said measurement apparatus communicates with said reader to receive said lot data file associated with said consumable reagent.

56. The measurement system of claim 55, wherein said reader is portable.

57. The measurement system of claim 55, wherein said measurement apparatus and said lot reader are configured to communicate wirelessly.

58. The measurement system of claim 55, wherein said reader is portable, and said measurement apparatus and said reader are configured to communicate wirelessly.

* * * * *

UNITED STATES PATENT AND TRADEMARK OFFICE

CERTIFICATE OF CORRECTION

PATENT NO. : RE44,345 E
APPLICATION NO. : 13/362011
DATED : July 9, 2013
INVENTOR(S) : Friedrich Karl Ackermann et al.

It is certified that error appears in the above-identified patent and that said Letters Patent is hereby corrected as shown below:

In the Specification:

Col. 6, Line 19, "one of the docking station 44 or 56" should read --one of the docking stations 44 or 56--;

Col. 6, Line 50, "example, however it is to be" should read --example, however, it is to be--;

Col. 7, Line 66, "quantity of test strip" should read --quantity of test strips--; and In the Claims:

Col. 15, Claim 50, Line 6, "The method if claim 27" should read --The method of claim 27--.

Signed and Sealed this
Twenty-seventh Day of May, 2014

Michelle K. Lee

Michelle K. Lee
*Deputy Director of the United States Patent and Trademark Office*